(12) United States Patent
Suzuki et al.

(10) Patent No.: US 8,480,870 B2
(45) Date of Patent: Jul. 9, 2013

(54) SENSOR ELEMENT AND GAS SENSOR

(75) Inventors: Yoshio Suzuki, Nagoya (JP); Kunihiko Nakagaki, Nagoya (JP); Yuji Okuda, Niwa-Gun (JP)

(73) Assignees: NGK Insulators, Ltd., Nagoya (JP); NGK Optoceramics Co., Ltd., Komaki (JP)

( * ) Notice: Subject to any disclaimer, the term of this patent is extended or adjusted under 35 U.S.C. 154(b) by 0 days.

(21) Appl. No.: 13/412,026

(22) Filed: Mar. 5, 2012

(65) Prior Publication Data

US 2012/0159771 A1    Jun. 28, 2012

Related U.S. Application Data

(63) Continuation of application No. 12/410,693, filed on Mar. 25, 2009, now abandoned.

(30) Foreign Application Priority Data

Mar. 27, 2008    (JP) .................................. 2008-083637

(51) Int. Cl.
    *G01N 27/26*    (2006.01)
(52) U.S. Cl.
    USPC ................ 204/426; 204/424; 29/592; 73/760
(58) Field of Classification Search
    USPC .................. 204/424, 426; 29/592; 73/760
    See application file for complete search history.

(56) References Cited

U.S. PATENT DOCUMENTS

| | | | |
|---|---|---|---|
| 5,671,054 A * | 9/1997 | Iwasaki ........................ | 356/631 |
| 5,672,811 A | 9/1997 | Kato et al. | |
| 5,897,723 A | 4/1999 | Tatumoto et al. | |
| 6,746,586 B2 * | 6/2004 | Kuroki et al. ................. | 204/429 |
| 7,105,070 B2 * | 9/2006 | Tosa et al. .................. | 156/89.12 |
| 2008/0105545 A1 | 5/2008 | Nakagaki et al. | |

FOREIGN PATENT DOCUMENTS

| | | |
|---|---|---|
| JP | 08-271476 A1 | 10/1996 |
| JP | 2003-075397 A1 | 3/2003 |
| JP | 2003-258424 A1 | 9/2003 |
| JP | 2003-344348 A1 | 12/2003 |
| JP | 2004-037473 A1 | 2/2004 |
| JP | 2004-117099 A1 | 4/2004 |
| JP | 2005-106691 | 4/2005 |
| JP | 2006-201023 A1 | 8/2006 |
| WO | 2007/025366 A1 | 2/2007 |
| WO | 2008/007706 A1 | 1/2008 |

\* cited by examiner

*Primary Examiner* — Luan Van
*Assistant Examiner* — Louis Rufo
(74) *Attorney, Agent, or Firm* — Burr & Brown (57) ABSTRACT

A gas sensor element, wherein an amount of flexure in a first section extending in a longitudinal direction of the sensor element from the position $8/27$ of a size of the element apart from one end of the element to the other end, is set to be greater than or equal to $1/1360$ and less than or equal to $1/670$ with respect to the size in the longitudinal direction of the element. The amount of flexure is a sum of a distance from a regression line to an upper side maximum displacement point and a distance from the regression line to a lower side maximum displacement point when calculating the regression line representing the relation of the position X in the longitudinal direction of the element and the displacement Y in a thickness direction from a plurality of data sets showing the relation of position X and displacement Y.

7 Claims, 7 Drawing Sheets

SENSOR ELEMENT AND GAS SENSOR

CROSS REFERENCE TO RELATED APPLICATIONS

This application is a continuation of U.S. application Ser. No. 12/410,693 filed Mar. 25, 2009, and claims the benefit under 35 USC §119(a)-(d) of Japanese Application No. 2008-083637 filed Mar. 27, 2008, the entireties of which are incorporated herein by reference.

FIELD OF THE INVENTION

The present invention relates to a sensor element used for detecting a predetermined gas component in a measurement gas in a gas sensor, such as a NOx sensor or an oxygen sensor, and to a gas sensor manufactured using such a sensor element.

BACKGROUND OF THE INVENTION

Conventionally, various measuring devices have been used for determining a concentration of a desired gas component in a measurement gas. A known device of measuring a NOx concentration in a measurement gas such as a combustion gas, for example, is a sensor having a Pt-containing electrode and a Rh-containing electrode formed on an oxygen ion conductive solid electrolyte layer, such as zirconia ($ZrO_2$) (see Japanese Patent Application Laid-Open No. 8-271476 and Japanese Patent Application Laid-Open No. 2004-37473, for example).

A sensor element used for detecting a predetermined gas component in a measurement gas in a gas sensor as disclosed in Japanese Patent Application Laid-Open No. 8-271476 or Japanese Patent Application Laid-Open No. 2004-37473 is manufactured by forming a predetermined circuit pattern on each of the plurality of ceramics green sheets including zirconia, which is an oxygen ion conductive solid electrolyte, as a ceramics component, by a screen printing or the like, laminating and integrating the plurality of ceramics green sheets to obtain a laminated body which is cut into an unit of element, and then burning.

The ceramics green sheets are subjected to various processes to manufacture the sensor element, as described the above. Therefore, deformation such as flexure or distortion caused by the process in manufacturing steps may be generated in the manufactured sensor element.

Specifically, a piece of the laminated body which has been cut into an unit of element (sensor element before burning) is to be shrunk by burning (burning shrinkage). This burning shrinkage is larger than shrinkage generated in other steps (e.g., a step of printing a circuit pattern on a ceramics green sheet, a step of drying after printing step or the like). Therefore, in the burning step of the steps of manufacturing the sensor element, deformation such as flexure or distortion is generated more easily than in other steps.

In the case where large deformation is generated in the manufactured sensor element due to shrinkage in the burning step or the like, the gas sensor manufactured using the sensor element may not be assembled accurately, or the measurement accuracy of the sensor may be affected. Deformation of the sensor element generated by burning shrinkage or the like is one of the causes of yield deterioration in manufacturing the sensor element and the gas sensor.

On the other hand, when actually used by being mounted on an emission system of an internal combustion in an automobile engine or the like, the gas sensor manufactured with the sensor element is going to be shocked due to various causes. The gas sensor needs strength against shock above a certain level (hereinafter, also referred to merely as strength) so as not to be damaged by such shock.

SUMMARY OF THE INVENTION

The present invention relates to a gas sensor used for detecting a predetermined gas component in a measurement gas, more specifically to a sensor element thereof.

The gas sensor of the present invention includes a long plate-like sensor element for detecting a predetermined gas component in a measurement gas. The sensor element includes a gas inlet provided at an end portion in a longitudinal direction of the sensor element for taking the measurement gas from an external space into the sensor element, wherein an amount of flexure which is a parameter for representing the extent of flexure in a thickness direction is specified by the following definition (a): (a) in the case of calculating a regression line representing the relation of a position X in the longitudinal direction and a displacement Y in the thickness direction of the sensor element in a target section from a plurality of data sets showing the relation of the position X and the displacement Y thereby to illustrate a plurality of data points representing the plurality of data sets and the regression line on a X-Y plane, and letting a data point which distance from the regression line is maximum at an upper side and a lower side of the regression line among the plurality of data points be an upper side maximum displacement point and a lower side maximum displacement point, respectively, the amount of flexure is a sum of a distance from the regression line to the upper side maximum displacement point and a distance from the regression line to the lower side maximum displacement point, and the amount of flexure in the first section specified in accordance with the definition (a) is greater than or equal to $1/1360$ and less than or equal to $1/670$ to a size in the longitudinal direction of the sensor element, the first section reaching to the other end portion of the sensor element from a position of $8/27$ in a size of the sensor element from the end portion in the longitudinal direction of the sensor element.

According to the above, the sensor element having great strength, in which the flexure in the thickness direction of the sensor element is suppressed, can be obtained by setting the amount of flexure in the first section of the sensor element within a preferable range on the basis of the size in the longitudinal direction of the sensor element.

It is therefore an object of the present invention to provide a sensor element having great strength, in which deformation in manufacturing does not affect accuracy of assembling a gas sensor, and a gas sensor including thereof

DETAILED DESCRIPTION OF THE INVENTION

Outline of Configuration of Gas Sensor

Figure 1:
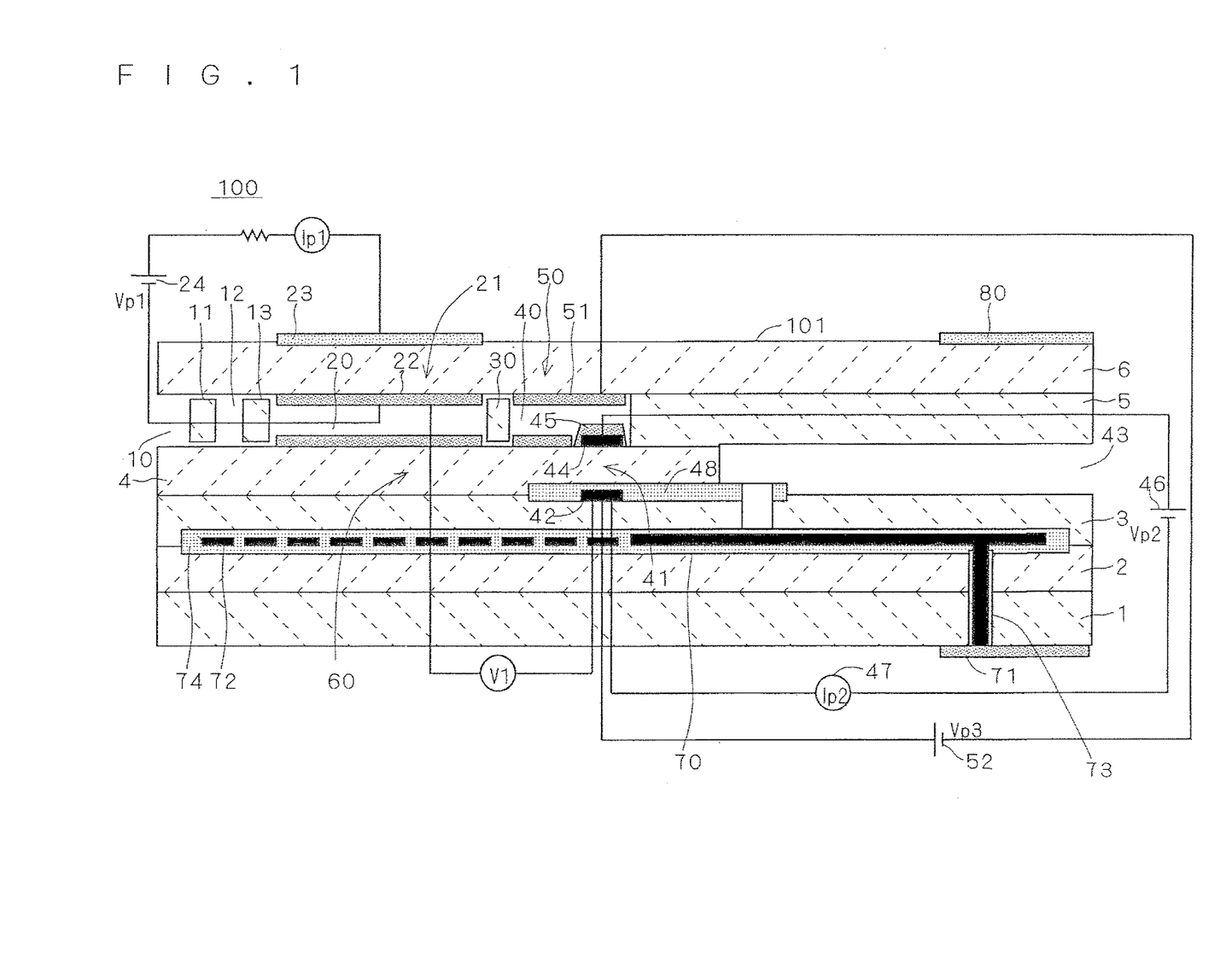
FIG. 1 is a sectional schematic view for showing a configuration of a gas sensor 100.

FIG. 1 is a sectional schematic view for showing a configuration of a gas sensor 100 according to a preferred embodiment of the invention. The gas sensor 100 detects a predetermined gas component in a gas which is an object of measurement (a measurement gas), and further, measures a concentration thereof. The present embodiment will be described taking an example where the gas sensor 100 is a NOx sensor detecting nitrogen oxide (NOx) as an object component, but the gas sensor of the present invention is applicable to a gas sensor having a gas component other than NOx as the object of measurement. The gas sensor 100 includes a sensor element 101 consisted of an oxygen ion conductive solid electrolyte such as zirconia ($ZrO_2$).

The sensor element 101 shown in FIG. 1 is an elongated and long plate-like element, including a structure of laminating a first substrate layer 1, a second substrate layer 2, a third substrate layer 3, a first solid electrolyte layer 4, a spacer layer 5, and a second solid electrolyte layer 6 in this order from a bottom seen in FIG. 1, each of the layers being consisted of an oxygen ion conductive solid electrolyte. The sensor element 101 is manufactured, for example, by performing a predetermined processing and pattern printing on ceramics green sheets corresponding to each layer, then laminating and burning them, as described above.

A gas inlet 10, a first diffusion control part 11, a buffer space 12, a second diffusion control part 13, a first internal space 20, a third diffusion control part 30 and a second internal space 40 are adjacently formed in this order in communication with one another between a lower surface of the second solid electrolyte layer 6 and an upper surface of the first solid electrolyte layer 4 at an end of the sensor element 101. The gas inlet 10, the buffer space 12, the first internal space 20 and the second internal space 40 are provided by hollowing out the spacer layer 5, which is a space with an upper portion sectioned by the lower surface of the second solid electrolyte layer 6, an lower portion sectioned by the upper surface of the first solid electrolyte layer 4, and a side portion sectioned by a side surface of the spacer layer 5. Each of the first diffusion control part 11, the second diffusion control part 13 and the third diffusion control part 30 is provided as two horizontally long slits (with an opening having a longitudinal direction in a direction perpendicular to FIG. 1). A part from the gas inlet 10 to the second internal space 40 is also referred to as a gas distribution part (also, a region including the gas inlet 10, the buffer space 12, the first internal space 20 and the second internal space 40 is referred to as a cavity part).

A reference gas inlet space 43 is provided between an upper surface of the third substrate layer 3 and a lower surface of the spacer layer 5 at a position which is far from the end than the gas distribution part is. The reference gas inlet space 43 is a space with an upper portion sectioned by the lower surface of the spacer layer 5, a lower portion sectioned by the upper surface of the third substrate layer 3, and a side portion sectioned by a side surface of the first solid electrolyte layer 4. For example, air is introduced to the reference gas inlet space 43 as a reference gas.

The gas inlet 10 is a portion which is open to the external space, and a measurement gas is brought into the sensor element 101 from the external space therethrough.

The first diffusion control part 11 provides a predetermined diffusion resistance to the measurement gas brought into from the gas inlet 10.

The buffer space 12 is provided in order to counteract concentration fluctuation of the measurement gas caused by pressure fluctuation (pulsation of exhaust pressure if a measurement gas is an emission gas of automobiles) of the measurement gas in the external space.

The second diffusion control part 13 provides a predetermined diffusion resistance to the measurement gas brought into the second diffusion control part 13 from the buffer space 12.

The first internal space 20 is provided as a space for controlling oxygen partial pressure in the measurement gas introduced through the second diffusion control part 13. The oxygen partial pressure is controlled by operating a main pump cell 21.

The main pump cell 21 is an electrochemical pump cell composed of an inside pump electrode 22 provided on an almost whole surface in a part of the lower surface of the second solid electrolyte layer 6 facing the first internal space 20, an outside pump electrode 23 provided in a region corresponding to the inside pump electrode 22 on an upper surface of the second solid electrolyte layer 6 to be exposed to the external space, and a part of the second solid electrolyte layer 6 interposed between those electrodes. The inside pump electrode 22 and the outside pump electrode 23 are formed as porous cermet electrodes (e.g. cermet electrodes of Pt including Au by 1% and $ZrO_2$) which are oblong in a plane view. Further, the inside pump electrode 22 is formed using material in which reduction ability to an NO component in the measurement gas is weakened, or material without reduction ability.

The main pump cell 21 is provided with a variable power source 24 outside the sensor element 101. The variable power source 24 applies a desired pump voltage Vp1 between the inside pump electrode 22 and the outside pump electrode 23 to flow pump current Ip1 in a positive direction or a negative direction between the outside pump electrode 23 and the inside pump electrode 22, allowing to pump out oxygen in the first internal space 20 to the external space or to pump in oxygen in the external space into the first internal space 20.

The third diffusion control part 30 provides a predetermined diffusion resistance to the measurement gas brought into the second internal space 40 from the first internal space 20.

The second internal space 40 is provided as a space for performing a process to measure concentration of nitrogen oxide (NOx) in the measurement gas introduced through the third diffusion control part 30. A NOx concentration can be measured by operating a measuring pump cell 41.

The measuring pump cell 41 is an electrochemical pump cell composed of a reference electrode 42 between the upper surface of the third substrate layer 3 and the first solid electrolyte layer 4, a measuring electrode 44 provided on the upper surface of the first solid electrolyte layer 4 facing the second internal space 40, spaced apart from the third diffusion control part 30, and the first solid electrolyte layer 4. Each of the reference electrode 42 and the measuring electrode 44 is a porous cermet electrode which is substantially oblong in a plane view. The reference electrode 42 is surrounded by an air induction layer 48 consisted of porous alumina and leading to a reference gas introduction space. The measuring electrode 44 is composed of metal obtained by resolving NOx which is a measurement gas component, and of porous cermet consisted of zirconia. Therefore, the measuring electrode 44 serves as a NOx reduction catalyst for resolving NOx in the atmosphere of the second internal space 40.

The measuring electrode 44 is covered with a fourth diffusion control part 45. The fourth diffusion control part 45 is a film composed of a porous body including alumina as a main component, and functions to limit the amount of NOx flowing into the measuring electrode 44.

The measuring pump cell 41 is provided with a DC power source 46 applying a pump voltage Vp2 which is a fixed voltage between the measuring electrode 44 and the reference electrode 42 to resolve NOx. The oxygen generated thereby in the atmosphere inside the second internal space 40 can be pumped out to the reference gas inlet space 43. A pump current Ip2 allowed to flow by the operation of the measuring pump cell 41 can be detected by an ammeter 47.

Also, with respect to the measurement gas introduced through the third diffusion control part 30, oxygen partial pressure is previously controlled in the first internal space 20, and thereafter, the oxygen partial pressure is further controlled in the second internal space 40 by an auxiliary pump cell 50. Accordingly, the gas sensor 100 can perform the measurement of a NOx concentration with high accuracy.

The auxiliary pump cell 50 is an electrochemical pump cell composed of an auxiliary pump electrode 51 provided on a substantially whole surface in a part of the lower surface of the second solid electrolyte layer 6 facing the second internal space 40, the second solid electrolyte layer 6, the spacer layer 5, the first solid electrolyte layer 4 and the reference electrode 42.

Similarly to the inside pump electrode 22, the auxiliary pump electrode 51 is formed using material in which reduction ability to an NO component in the measurement gas is weakened, or material without reduction ability.

The auxiliary pump cell 50 is provided with a DC power source 52 outside the sensor element 101. The DC power source 52 applies a fixed voltage Vp3 between the auxiliary pump electrode 51 and the reference electrode 42 to pump out oxygen in the atmosphere inside the second internal space 40 into the reference gas inlet space 43.

The sensor element 101 includes an oxygen partial pressure detecting sensor cell 60 which is an electrochemical pump cell composed of the inside pump electrode 22, the reference electrode 42, the second solid electrolyte layer 6, the spacer layer 5 and the first solid electrolyte layer 4.

The oxygen partial pressure detecting sensor cell 60 can detect oxygen partial pressure in the atmosphere of the first internal space 20 based on an electromotive force V1 generated between the inside pump electrode 22 and the reference electrode 42 which is caused by the difference of oxygen concentration between the atmosphere of the first internal space 20 and a reference gas (air) of the reference gas inlet space 43. The detected oxygen partial pressure is used for feedback controlling the variable power source 24. Specifically, a pump voltage applied to the main pump cell 21 is controlled so as to set oxygen partial pressure in the atmosphere of the first internal space 20 at a predetermined value which is lower enough to control oxygen partial pressure in the second internal space 40.

Moreover, the sensor element 101 includes a heater 70 which functions to control temperature for heating the sensor element 101 and keeping it warm in order to enhance oxygen ion conductivity of solid electrolyte. The heater 70 includes a heater electrode 71, a heater 72 and a through hole 73 and a heater insulating layer 74.

The heater electrode 71 is provided near the end portion of the element at a side of the reference gas inlet space 43 on a lower surface of the first substrate layer 1. The heater electrode 71 is connected to the external power source to supply electricity to the heater 70 from outside.

The heater 72 is an electrical resistor formed to be interposed between the second substrate layer 2 and the third substrate layer 3 from above and below. The heater 72 is connected to the heater electrode 71 via the through hole 73, and produces heat by feeding from outside through the heater electrode 71 to heat solid electrolyte forming solid electrolyte layers and keep it warm.

The heater 72 is buried over the whole area from the first internal space 20 to the second internal space 40 so that the entire area of the sensor element 101 is heated and kept warm at a temperature to activate the solid electrolyte.

The heater insulating layer 74 formed of an insulator such as alumina or the like is provided on an upper surface and a lower surface of the heater 72 in order to obtain electronic insulation among the second substrate layer 2, and the third substrate layer 3, and the heater 72, that is, electronic insulation between each electrode of the sensor element 101 and the heater 72.

The sensor element 101 includes connector electrodes 80 formed near the end of the element at the side of the reference gas inlet space 43 on the upper surface of the second solid electrolyte layer 6.

Each of the connector electrodes 80 is connected to an electrode of the sensor element 101 (the inside pump electrode 22, the outside pump electrode 23, the reference electrode 42, the measuring electrode 44 and the auxiliary pump electrode 51) (each connection is not shown in Figure). Detection of voltage applied between each of these electrodes and current flowing in each electrode is controlled from outside the sensor element 101 through the connector electrodes 80.

In use of the gas sensor 100, the pump voltage Vp1, Vp2 and the pump current Ip1, and the detection of the electromotive force V1 and the pump current Ip2 are controlled from outside the sensor element 101 through the connector electrodes 80.

In manufacturing the gas sensor 100 using the sensor element 101, connector parts for connecting the connector electrodes 80 to outside the sensor element 101 is connected to the connector electrodes 80 (or to the connector electrodes 80 and the heater electrode 71) in a manner of making contacts each other.

In the gas sensor 100 having the aforementioned configuration, the measurement gas is provided to the measuring pump cell 41, with oxygen partial pressure constantly maintained at fixed low value (a value substantially not affecting the measurement of NOx) by operating the main pump cell 21 and the auxiliary pump cell 50. Accordingly, the pump current Ip2 is to be proportional to the reduced NOx concentration, the pump current Ip2 flowing in the measuring pump cell 41 by pumping out oxygen generated by a reduction of NOx.

Dimension of Sensor Element

Figure 2:
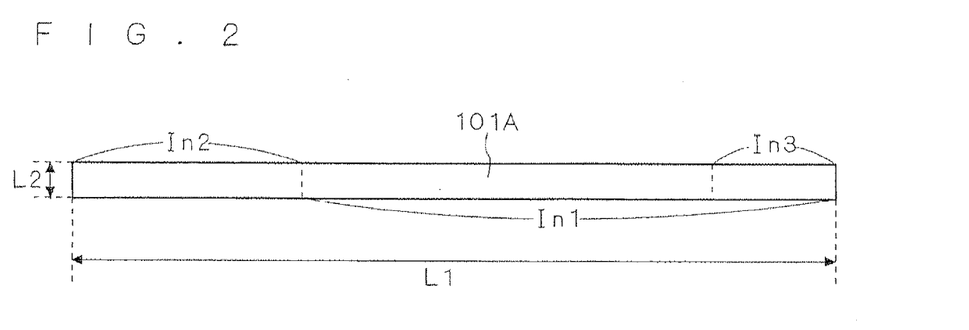
FIG. 2 is a side view of a sensor element 101 for showing dimension of main parts of the sensor element 101.

Next, dimension of the main part of the sensor element 101 will be described referring to FIGS. 2 and 3. FIG. 2 is a side view of the sensor element 101 (an element surface 101A) seen from the same direction as FIG. 1.

In FIG. 2, a size L1 is a length in a longitudinal direction of the sensor element 101. The size L1 of the sensor element 101 is 67.0±5.0 mm.

A size L2 is a thickness of the sensor element 101. The thickness of the sensor element 101 represents a distance from the lower surface of the first substrate layer 1 to the upper surface of the second solid electrolyte layer 6 in FIG. 1. The size L2 of the sensor element 101 is 1.4±1.0 mm.

In the present embodiment, when evaluating the extent of flexure of the sensor element 101 (details will be described later), the sensor element 101 is sectionalized into three sections of the first section In1, the second section In2 and the third section In3, considering the structure of the sensor element 101 and the contact points between the parts used for manufacturing the gas sensor 100 using the sensor element 101 and the sensor element 101.

The first section In1 includes the places where the parts used for manufacturing the gas sensor 100 using the sensor element 101 makes contacts on the surface of the sensor element 101, wherein the parts is for fixing the sensor element 101 at a predetermined position of the gas sensor 100 (gas sealing material for sealing and fixing), or for electrically connecting the sensor element 101 to outside (connector parts for connecting the connector electrode 80 and the heater electrode 71 to outside the sensor element 101). The first section In1 is a section in the longitudinal direction of the sensor element 101 from a position 20 mm apart from the end at the side of the gas inlet 10, to the end at the side of the connector electrode 80.

The second section In2 includes the aforementioned gas distribution part (a portion from the gas inlet 10 to the second internal space 40), and does not make contacts with other parts in manufacturing the gas sensor 100. The second section In2 is a section in the longitudinal direction of the sensor element 101 from the end at the side of the gas inlet 10 to the end at the side of the connector electrode 80, having a distance of 20 mm.

The third section In3 is a section making contacts with the connector parts in the first section In1. That is, the third section In3 includes the connector electrodes 80 (and the heater electrode 71). The third section In3 of the sensor element 101 is the section in the longitudinal direction of the sensor element 101 from the end at the side of the connector electrode 80 to the end at the side of the gas inlet 10, having a distance of 10 mm.

Figure 3:
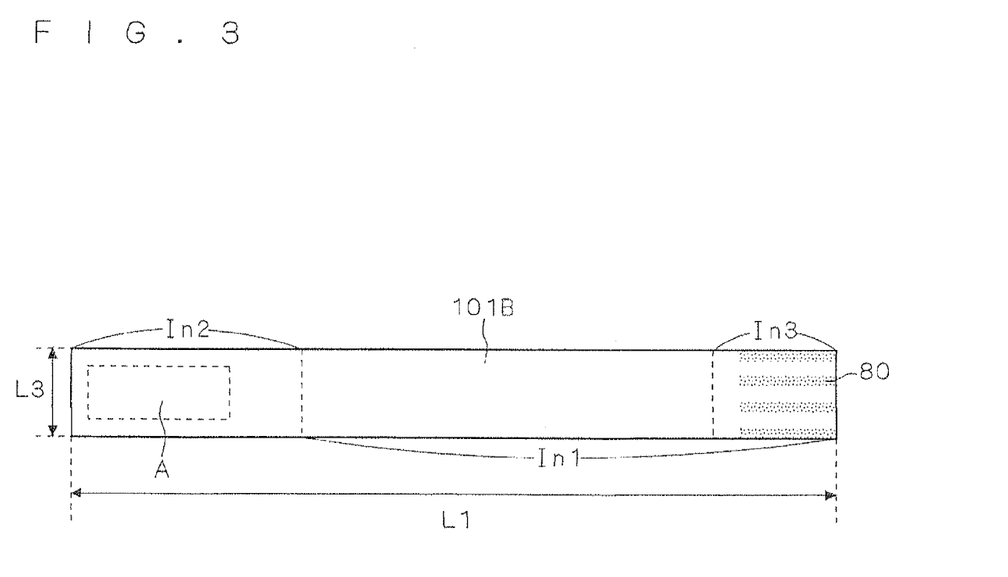
FIG. 3 is a plane view of the sensor element 101 for showing dimension of main parts of the sensor element 101.

FIG. 3 is a plane view (element surface 101B) of FIG. 2 seen from the side of the second solid electrolyte layer 6. The length L1 and L2 and the first section In1, the second section In2 and the third section In3 shown in FIG. 3 are similarly to what are shown in FIG. 2.

A size L3 is a width of the sensor element 101 as shown in FIG. 3. The width represents a length in a lateral direction of the sensor element 101 seen from above the first substrate layer 1. The size L3 of the sensor element 101 is 4.2±0.5 mm.

In FIG. 3, a region A includes the gas distribution part, and an approximate position of the gas distribution part is shown in FIG. 3. Each of the connector electrodes 80 is also shown in FIG. 3, and the heater electrode 71 is formed at the position corresponding to the connector electrodes 80 on the lower surface of the first substrate layer 1.

Displacement Measuring Device

Figure 4:
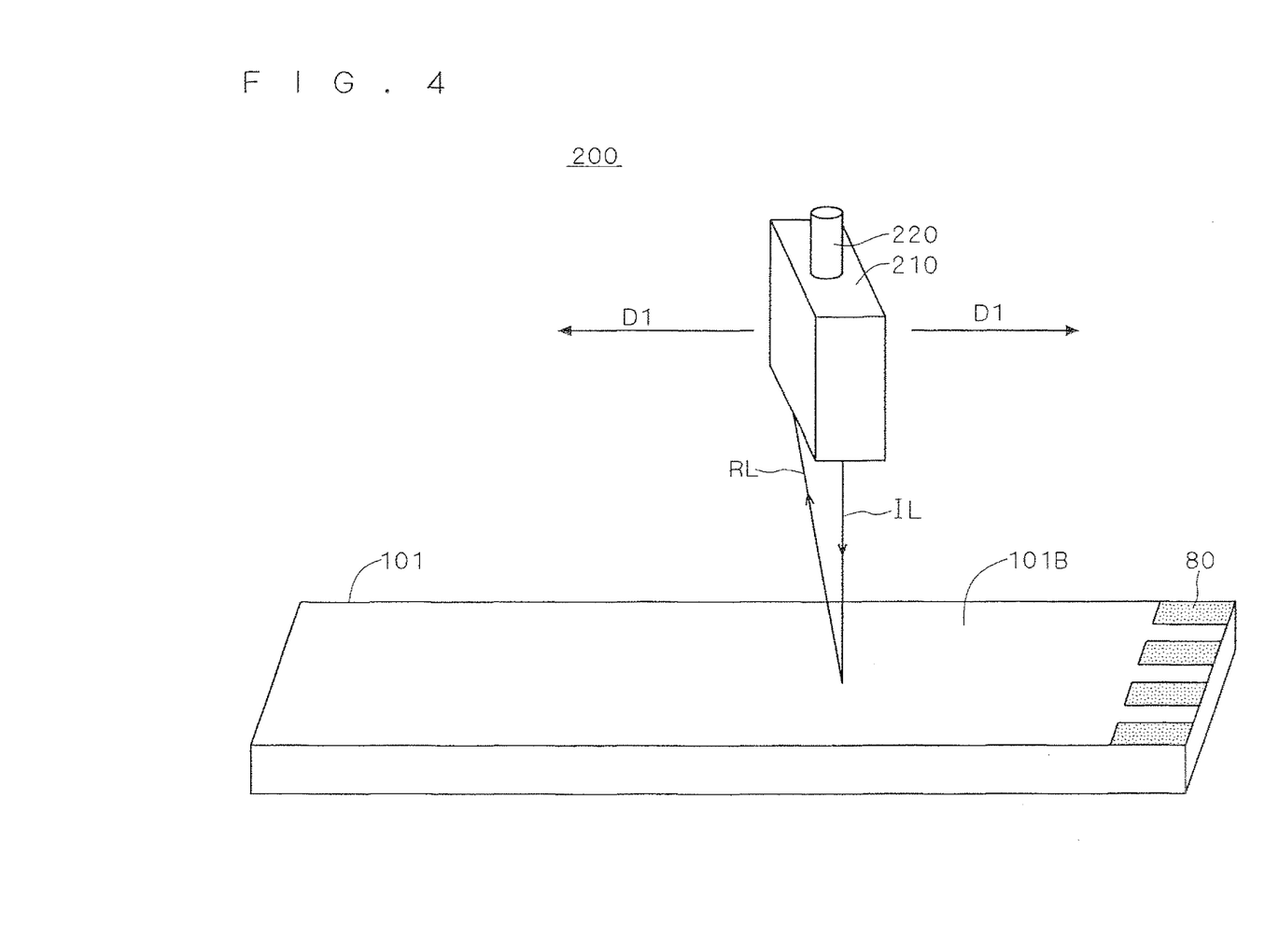
FIG. 4 is a schematic view of a configuration of a displacement measuring device 200.

Next, a displacement measuring device 200 for measuring displacement on the element surface 101B of the sensor element 101 will be described. Here, the case where the displacement measuring device 200 is a laser displacement gauge will be described as an example.

FIG. 4 is a schematic view of a configuration of the displacement measuring device 200. The displacement measuring device 200 is for measuring a distance between the element surface 101B and the head part 210, and includes mainly the head part 210, a measurement illuminant 220 and a horizontal drive structure (not shown).

The head part 210 is formed to be able to project and receive light for measuring displacement given from the measurement illuminant 220.

When measuring displacement, the head part 210 irradiates light for measuring, given from the measurement illuminant 220, to the element surface 101B, and at the same time, receives reflected light of the light for measuring from the element surface 101B. A distance from the head part 210 to the element surface 101B is calculated on the basis of the reflected light received by the head part 210.

In FIG. 4, light irradiated to the element surface 101 B is shown as IL, and light reflected and received by the head part 210 is shown as RL.

The measurement illuminant 220 and the head part 210 are integrally formed, and connected to the horizontal drive mechanism (not shown). The horizontal drive mechanism can move the head part 210 (and the measurement illuminant 220) horizontally in a direction D1 in FIG. 4 which is a direction parallel to the longitudinal direction of the sensor element 101.

The distance from the head part 210 to the element surface 101B can be measured along the longitudinal direction of the sensor element 101 using the above-described displacement measuring device 200. Displacement of the element surface 101B can be obtained from the obtained result of measurement, that is, an alteration of the distance from the head part 210 to the element surface 101B in the longitudinal direction of the element.

Figure 5:
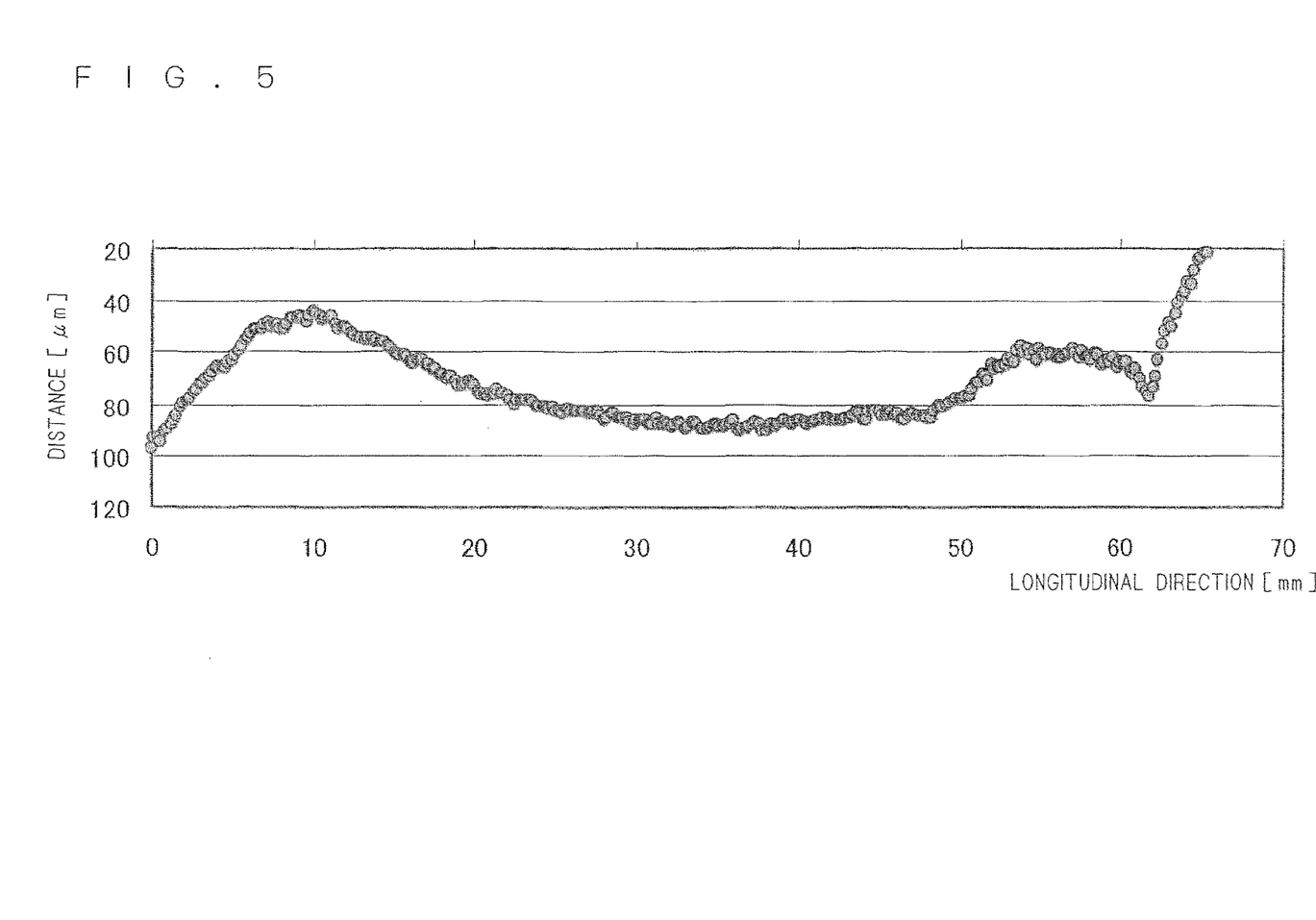
FIG. 5 is a view for showing an example of the result obtained by measuring a distance from an element surface 101B to a head part 210 with the displacement measuring device 200.

FIG. 5 is a view for showing an example of the result obtained by measuring the distance from the element surface 101B to the head part 210 with the displacement measuring device 200. In FIG. 5, the result of measuring the distance from the element surface 101B to the head part 210 with 20 μm interval in the longitudinal direction of the sensor element 101 by the displacement measuring device 200 is plotted. The axis of ordinate shows the distance from the head part 210 to the element surface 101B, and the axis of abscissas shows the position along the longitudinal direction of the sensor element 101. The position of 0 mm in the abscissa shows the end of the element at the side of the gas inlet 10, and the value of the abscissa shows the position nearer the end portion of the element at the side of the reference gas inlet space 43 as it gets larger (See In FIG. 5, displacement appears in the thickness direction of the sensor element 101, and such displacement is caused by differential shrinkage at the time of burning between the solid electrolyte composing the sensor element 101 and the other portions.

Method of Calculating the Amount of Flexure

Next, the method of calculating the amount for expressing the extent of flexure in the thickness direction of the sensor element 101 (hereinafter, also referred to as merely the amount of flexure) will be described.

The definition of "the amount of flexure" will be defined as follows.

The definition (a): 1) measuring the relation of X and Y, letting the position in the longitudinal direction of the sensor element in a targeted section be X, and the displacement in the thickness direction of the sensor element surface be Y, "the amount of flexure", 2) calculating a regression line with least square method from a scatter diagram in which the above measured data points are plotted on a X-Y plane with X and Y as two variables, 3) letting a data point of which distance from the regression line is maximum in the targeted section be an upper side maximum displacement point or a lower side maximum displacement point, in each region of the upper side and the lower side of the regression line on the X-Y plane, respectively, and 4) "the amount of flexure" is a sum of a distance from the regression line to the upper side maximum displacement point and a distance from the regression line to the lower side maximum displacement point.

In the preferred embodiment, the amount of flexure is calculated in each of the first section In1, the second section In2 and the third section In3.

The first section In1 includes the places where the parts for fixing the sensor element 101 at a predetermined position of the gas sensor 100 (gas sealing material), or the parts for electrically connecting the sensor element 101 to outside (connector parts) makes contacts on the surface of the sensor element 101. Thus, if the amount of flexure in the first section is more than a predetermined value, flexure stress may be caused due to contact of the parts with the element when assembling the gas sensor 100.

Then, since the second section In2 includes the gas distribution part (a portion from the gas inlet 10 to the second internal space 40), flexure dependent on such a space structure may be caused.

Furthermore, since the third section In3 is the one making contacts with the connector parts in the first section In1, if the amount of flexure is more than a predetermined value, defects such as breakage caused by stress may be caused.

Accordingly, it is necessary to set the amount of flexure in each of the first section In1, the second section In2 and the third section In3, calculated respectively, within an appropriate range in assembling the gas sensor 100.

Figure 6:
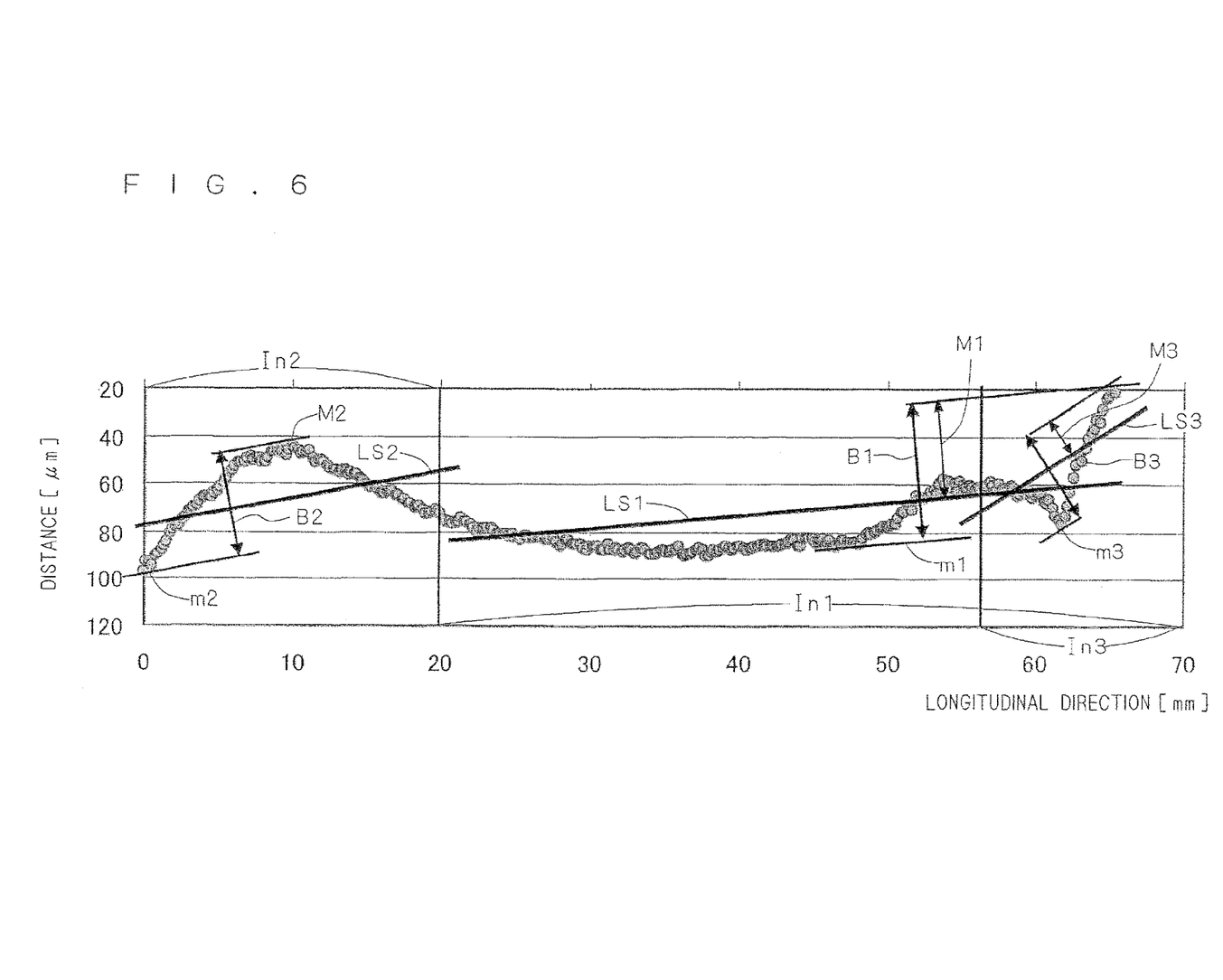
FIG. 6 is a view for illustrating a calculation method of the amount of flexure in each of the first, second and third sections.

FIG. 6 is a view for illustrating a calculation method of the amount of flexure in each of the first section In1, the second section In2 and the third section In3. The data points plotted in FIG. 6 are similar to those in FIG. 5.

The calculation method of the amount of flexure in each section will be described below. As for the first section In1, first, a regression line LS1 is calculated by least square method with respect to the data points. Subsequently, in the upper side region of the regression line LS1 between two regions divided by the regression line LS1 in FIG. 6, a distance from the data point in which the distance from the regression line LS1 is maximum (the upper side maximum displacement point), to the regression line LS1 is set to be M1, and in the lower side region, a distance from the data point in which the distance from the regression line LS1 is maximum (the lower side maximum displacement point), to the regression line LS1 is set to be m1. The amount of flexure B1 (the amount of flexure in the first section) is calculated using the sum of these distances M1 and m1 as:

$$B1=M1+m1.$$

Similarly to the calculation of the amount of flexure B1 for the first section In1, for the second section In2, a regression line LS2 is calculated by least square method with respect to the data points in the second section In2. Subsequently, in the upper side region of the regression line LS2 between two regions divided by the regression line LS2 in FIG. 6, a distance from the data point in which the distance from the regression line LS2 is maximum (the upper side maximum displacement point), to the regression line LS2 is set to be M2, and in the lower side region, a distance from the data point in which the distance from the regression line LS2 is maximum (the lower side maximum displacement point), to the regression line LS2 is set to be m2. The amount of flexure B2 (the amount of flexure in the second section) is calculated using the sum of these distances M2 and m2 as:

$$B2=M2+m2.$$

Similarly to the calculation of the amount of flexure for the first section In1 and for the second section In2, for the third section In3, a regression line LS3 is calculated by least square method with respect to the data points in the second section In3. Subsequently, in the upper side region of the regression line LS3 between two regions divided by the regression line LS3 in FIG. 6, a distance from the data point in which the distance from the regression line LS3 is maximum (the upper side maximum displacement point), to the regression line LS3 is set to be M3, and in the lower side region, a distance from the data point in which the distance from the regression line LS3 is maximum (the lower side maximum displacement point), to the regression line LS3 is set to be m3. The amount of flexure B3 (the amount of flexure in the third section) is calculated using the sum of these distances M3 and m3 as:

$$B3=M3+m3.$$

The amount of flexure B1 in the first section In1, the amount of flexure B2 in the second section In2 and the amount of flexure B3 in the third section In3 are needed to be set within a preferable range, respectively, so that the sensor element 101 makes good contacts and connection with parts needed in these sections, or so that any interference of the sensor element 101 with other parts is not caused (that is, in order not to deteriorate the accuracy of assembly), when manufacturing the gas sensor 100. In the gas sensor 100, such preferable range of the amount of flexure B1 in the first section In1 is set to be less than or equal to 0.6 mm, the amount of flexure B2 in the second section In2 is set to be less than or equal to 1.05 mm, and the amount of flexure B3 in the third section In3 is set to be less than or equal to 0.24 mm.

Relation of the Amount of Flexure and Strength to Falling

Next, the relation of the amount of flexure in the first section and strength to falling of the sensor element 101 will be described. Such relation is evaluated by the test described below.

First, the amount of flexure in the first section is calculated by the above-described method in the sensor element 101. Subsequently, the gas sensor 100 is manufactured using the sensor element 101 whose the amount of flexure B1 has been calculated. The gas sensor 100 is manufactured by fixing the sensor element 101 with the gas sealing material, connecting the connector electrodes 80 (and the heater electrode 71) of the sensor element 101 to the connector parts, and further making a casing.

Next, a shock is applied to the gas sensor 100 (and the sensor element 101) whose the amount of flexure B1 has already been obtained by dropping it from a predetermined height.

After being dropped, a condition of the sensor element 101 is evaluated in the gas sensor 100. Specifically, determination is made whether the sensor element 101 is broken or not, and whether cracks and damages resulting in remarkable deterioration of measurement accuracy for a sensor are caused or not.

The above determination is made to the gas sensors 100, each of which includes the sensor element 101 having varied amount of flexure B1 by dropping them from various heights. It can be said that the larger the height of falling is at which the sensor element 101 is broken, or cracks and damages are caused, the greater strength to falling the sensor element 101 has.

Figure 7:
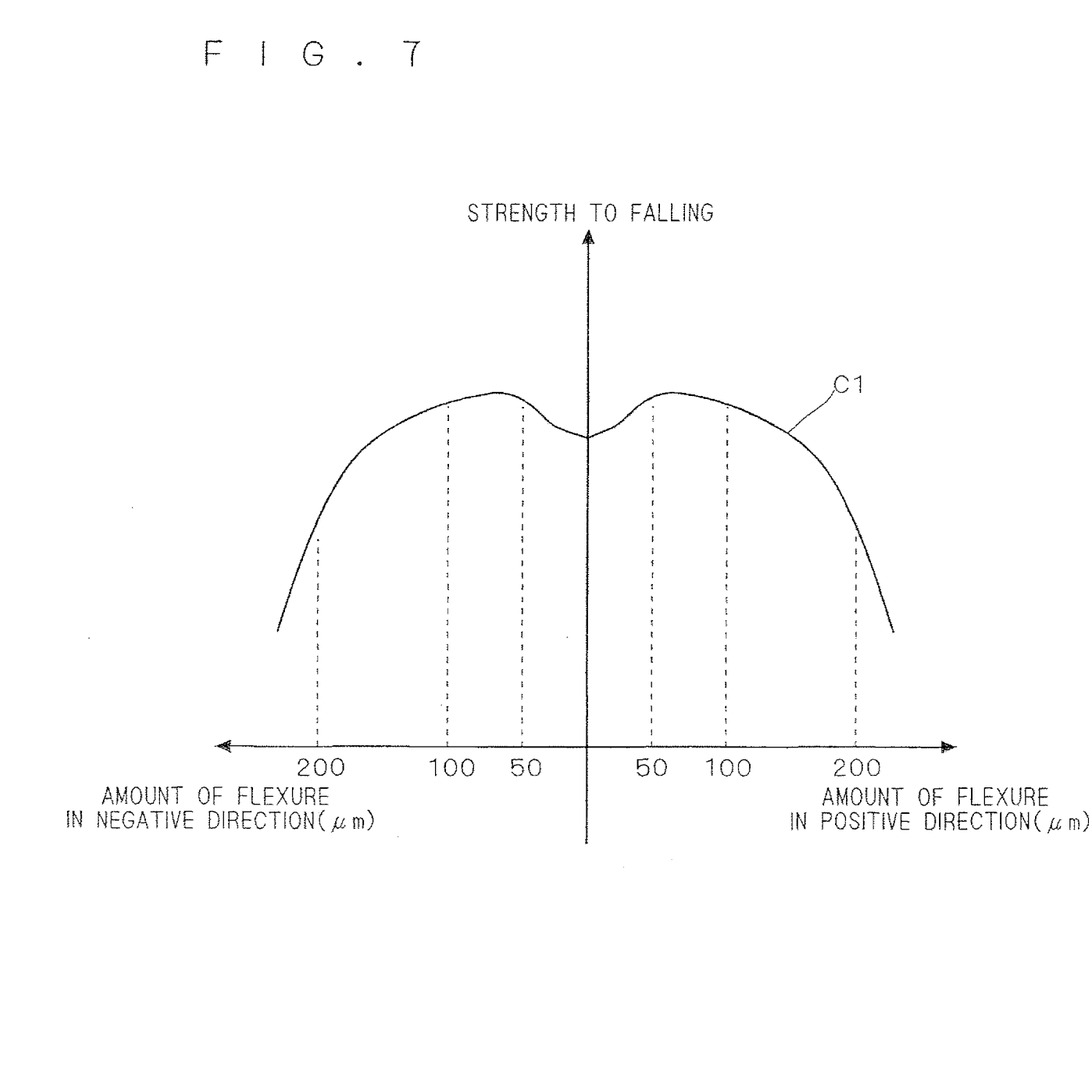
FIG. 7 is a view for showing the relation of the amount of flexure in the first section and strength to falling.

FIG. 7 shows the result obtained form the above test, and a curved line C1 indicates the relation of the amount of flexure B1 in the first section and the strength to falling of the sensor element 101. In FIG. 7, the axis of abscissas shows the amount of flexure B1 of the sensor element 101.

The amount of flexure in a positive direction and the amount of flexure in a negative direction shown in the axis of abscissas of FIG. 7 are to distinguish a way of flexure because the flexure has its way of bend in the actual sensor element 101 even when the value of the amount of flexure B1 in the first section is same. This distinction is made depending on the way of flexure in a thickness direction (whether it is a bend at side of the electrode, or a bend at inside of the electrode). The inventors of the invention have confirmed that the curved line C1 draws a line to be almost symmetrical with respect to the axis of ordinate.

In FIG. 7, the axis of ordinate indicates the height (the average value of the height for a plurality of the gas sensors 100) for dropping the gas sensor 100 at which the sensor element 101 is broken, and cracks and damages resulting in remarkable deterioration of measurement accuracy for a sensor are caused. The strength to falling is more greater especially above the ordinate, as the higher the position for dropping at which cracks and damages are caused to the gas sensor 100, the greater the strength to falling the sensor element 101 has.

The curved line C1 of FIG. 7 shows the tendency that the smaller the amount of flexure B1 in the first section is, the greater the strength of the sensor element is. This is assumed to be because the larger the amount of flexure B1, the more convergent the shock applied to the gas sensor 100 (and the sensor element 101) is prone to be on a certain point of the sensor element 101.

Meanwhile, the curved line C1 shows the tendency that, while the strength to falling has a relative maximum in the range that the value of the amount of flexure B1 in the first section is from 100 μm to 50 μm, it becomes smaller as the amount of flexure B1 becomes smaller in the vicinity of the range from 50 μm to 0 μm.

This is assumed to be because, while the assembly parts hit the sensor element 100 almost vertically if the sensor element is straight, in the case there is a little amount of flexure, the angle is brought between the sensor element 101 and the assembly parts so that the shock is dispersed. Therefore, the sensor element 101 having the amount of flexure B1 in the first section from 50 μm to 100 μm in the vicinity of relative maximum has greater strength than the sensor element 101 having the amount of flexure B1 in the first section close to 0 μm.

Accordingly, the ratio of the amount of flexure B1 in the first section to the size in the longitudinal direction of the sensor element 101 (67.0±5.0 mm) is preferably greater than or equal to $1/1360$ and less than or equal to $1/670$ in order to obtain the high strength. Further, the ratio of the amount of flexure B1 in the first section to the thickness of the sensor element 101 (1.4±1.0 mm) is preferably greater than or equal to $5/72$ and less than or equal to $5/146$.

Based on the above, in the gas sensor 100, the range of the amount of flexure B1 in the first section is set to be less than or equal to 0.60 mm (less than or equal to $3/335$ with respect to the size in the longitudinal direction of the sensor element 101), the amount of flexure B2 in the second section is set to be less than or equal to 1.05 mm (less than or equal to $21/1340$ with respect to the size in the longitudinal direction of the sensor element 101), and the amount of flexure B3 in the third section is set to be less than or equal to 0.24 mm (less than or equal to $6/1675$ with respect to the size of the longitudinal direction of the sensor element 101). Furthermore, the amount of flexure B1 in the first section is set to be from 50 μm to 100 μm so that the gas sensor 100 is assembled with high precision, and becomes tough to the shock.

Control of the Amount of Flexure

Next, the method of controlling deformation of the sensor element 101 caused in burning shrinkage in order to obtain the amount of flexure having the aforementioned preferable range will be described.

First, flexure and distortion in the sensor element 101 due to burning shrinkage can be controlled and reduced by adjusting burning shrinkage of the respective parts of the sensor element 101, considering the size or material of members composing the sensor element 101 (e.g., electrodes such as the reference electrode 42 or the measuring electrode 44 and the like, and each solid electrolyte layer 1 to 6).

Furthermore, it is possible to reduce the deformation of the sensor element 101 due to burning shrinkage by burning the sensor element 101 with applying pressure on the surface of the sensor element 101 from before burning. In the present embodiment, the pre-burned sensor element 101 is placed on a plane and is burned, with a long bar W (hereinafter, referred to as a loading bar W) having a predetermined mass being placed at several points of the surface of the sensor element 101 (a surface which is to be an upper surface when burning). This makes it possible to control and suppress the deformation of the sensor element 101. The method of applying pressure is not limited to the placement of the loading bar W, but the position to apply pressure on the pre-burned sensor element 101 and the strength of the pressure can be experimentally specified so as to obtain the amount of flexure within the preferable range as described above.

Figure 8:
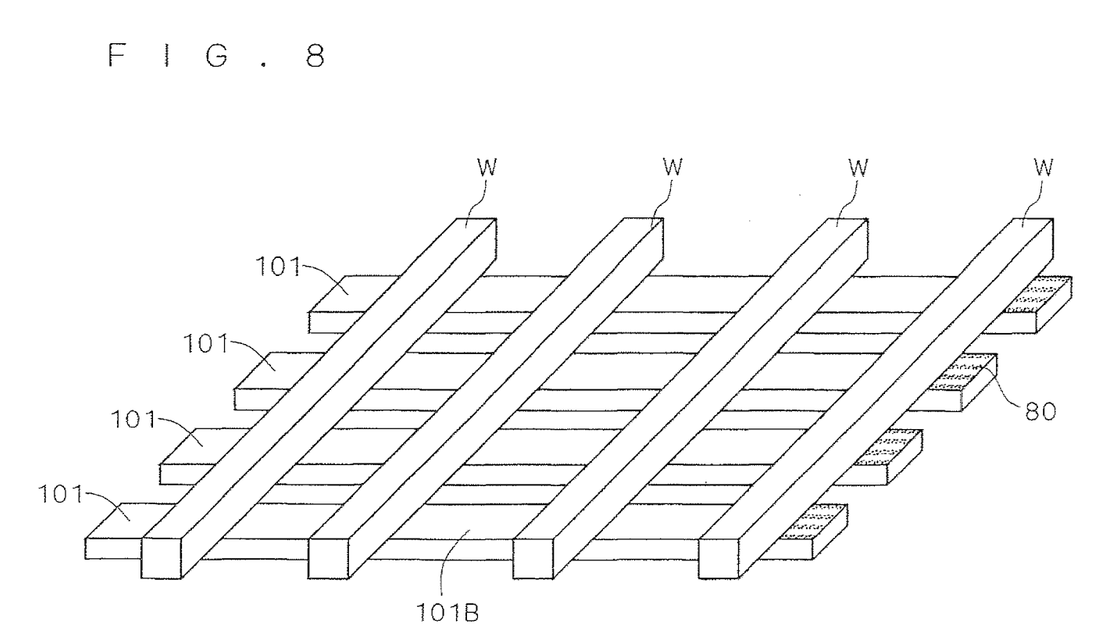
FIG. 8 is a view for showing one example of a way of placement of a loading bar W.

FIG. 8 is a view for illustrating the way of placing the loading bar W on the pre-burned sensor element 101. FIG. 8 illustrates the situation in which a plurality of the loading bars W are placed at predetermined positions with a predetermined interval on each element surface 101B of a plurality of the pre-burned the sensor elements 101 such that the longitudinal direction of each loading bar W is vertical to the longitudinal direction of each sensor element 101. FIG. 8 only shows an example of the placement of the loading bar W, and thus, the way of the placement is not limited to the above. The position and direction of placing the loading bar W may be appropriately controlled to put desired force on a desired position of the pre-burned the sensor element 101.

It is preferable to determine the position of placing the loading bar W so as to put a predetermined force, especially on the second section In2 including the first internal space 20 and the second internal space 40, the third section In3 including the through hole 73 and the connector electrodes 80 and the portion where the respective electrodes are formed. Since differential shrinkage with the solid electrolyte is easily caused in the portion which are not solid electrolyte, that is, the portion where the deformation of the element is to be large, it is preferable to place the loading bar W on this portion.

As described above, there are points on the surface of the sensor element 101 at which the parts used for manufacturing the gas sensor 100 with the sensor element 101 make contacts, wherein the parts is for fixing the sensor element 101 on the predetermined position of the gas sensor 100 (gas sealing material), or for electrically connecting the sensor element 101 to outside (connector parts) the surface of the sensor element 101. If the deformation is great at the above contact points with the gas sealing material or the connector parts in the sensor element 101, gap may be caused at the contact points between the parts and the sensor element 101, and the force may be centralized on a certain contact point in assembling the gas sensor 100. Meanwhile, the deformation of the sensor element 101 due to burning shrinkage can be suppressed by placing the loading bar W at these contact points, and further, allowing to improve the accuracy of assembly of the gas sensor 100.

Variation

As the placement method of the loading bar W other than the above described method, the loading bar W may be placed on each pre-burned sensor element 101 to cover the entire surface of the sensor element 101 so as to put force on the entire surface of the sensor element 101 uniformly. When the pre-burned sensor element 101 is burned with such method, it is possible to put force on the overall sensor element 101 so that the deformation of the entire sensor element 101 can be suppressed.

What is claimed:

1. A method of manufacturing a sensor element of a gas sensor for detecting a predetermined gas component in a measurement gas, said method comprising the steps of:
  i) laminating a plurality of ceramic green sheets respectively corresponding to said plurality of layers to form a laminated body;
  ii) cutting said laminated body into a plurality of element bodies; and
  iii) burning said plurality of element bodies to obtain a plurality of sensor elements, said sensor elements including a laminated structure of a plurality of layers, having a long plate shape, including a gas inlet located at one end portion in a longitudinal direction thereof for taking the measurement gas from an external space into an inside thereof, having a size in the longitudinal direction of 62 mm or greater and 72 mm or smaller, and including a plurality of electrodes comprising a measuring electrode,
  wherein when a portion between a first position with a spacing of 20 mm from an end surface on said one end portion side and an end surface on the other end portion side of said sensor is a first section in said longitudinal direction, and an amount of flexure which is a parameter for representing the extent of flexure in a thickness direction of said sensor element is specified by a definition (a) below, in said step (iii), burning is performed while applying a pressure on a surface of said element body such that the amount of flexure in said first section is greater than or equal to $1/1360$ and less than or equal to $1/670$ of the size in the longitudinal direction of said sensor element,
  definition (a): in the case of calculating a regression line representing the relation of a position X in the longitudinal direction and a displacement Y in said thickness direction of said sensor element in a target section from a plurality of data set showing the relation of said position X and said displacement Y thereby to illustrate a plurality of data points representing said plurality of data sets and said regression line on an X-Y plane, and letting data points with a maximum distance from said regression line at an upper side and a lower side of said regression line among said plurality of data points be an upper side maximum displacement point and a lower side maximum displacement point, respectively, said amount of flexure is a sum of a distance from said regression line to said upper side maximum displacement point and a distance from said regression line to said lower side maximum displacement point.

2. The method of manufacturing a sensor element according to claim 1, wherein
  in said step iii), burning is performed while applying a pressure on said surface of said element body such that the amount of flexure in said first section is greater than or equal to $5/72$ and less than or equal to $5/146$ of the thickness of said sensor element.

3. The method of manufacturing a sensor element according to claim 1, wherein
  when a portion between the end surface on said one end portion side and said first position is a second section and a portion between the end surface on said other end portion side and a second position with a spacing of 10 mm from the end surface on said other end portion side is a third section in the longitudinal direction of said sensor element, in said step iii), burning is performed while applying a pressure on said surface of said element body such that:
  the amount of flexure in said second section specified in accordance with said definition (a) for said second section as said target section is less than or equal to $21/1340$ of the size in the longitudinal direction of said sensor element, and
  the amount of flexure in said third section specified in accordance with said definition (a) for said third section as said targeting section is less than or equal to $6/1675$ of the size in the longitudinal direction of said sensor element.

4. The method of manufacturing a sensor element according to claim 1, wherein
  in said step iii), a pressure is applied on said surface by placing a pressure member with a predetermined mass on said surface of said element body.

5. The method of manufacturing a sensor element according to claim 3, wherein
  in said step iii), a pressure member with a predetermined mass is placed at positions on said surface of said element body, said positions corresponding to said second section and said third section.

6. The method of manufacturing a sensor element according to claim 4, wherein
  in said step iii), said pressure member is placed at a position on said surface of said element body, at which said pressure member comes into contact with an external member in assembling a gas sensor including said sensor element.

7. The method of manufacturing a sensor element according to claim 5, wherein
  in said step iii), said pressure member is placed at a position on said surface of said element body, at which said pressure member comes into contact with an external member in assembling a gas sensor including said sensor element.

* * * * *